US006938482B2

United States Patent
Schultz

(10) Patent No.: US 6,938,482 B2
(45) Date of Patent: Sep. 6, 2005

(54) HUMIDITY SENSOR ELEMENT CONTAINING POLYPHENYLSULFONE

(75) Inventor: Gerald Schultz, Brookline, MA (US)

(73) Assignee: General Electric Co., Plainville, CT (US)

(*) Notice: Subject to any disclaimer, the term of this patent is extended or adjusted under 35 U.S.C. 154(b) by 0 days.

(21) Appl. No.: 10/250,084

(22) Filed: Jun. 3, 2003

(65) Prior Publication Data

US 2004/0244482 A1 Dec. 9, 2004

(51) Int. Cl.[7] .................................................. G01N 7/00
(52) U.S. Cl. ................... 73/335.01; 73/29.01; 73/29.05; 73/31.05; 422/88
(58) Field of Search ..................... 73/335.01, 29.01, 73/29.05, 31.05; 422/88

(56) References Cited

U.S. PATENT DOCUMENTS

| 3,350,941 | A | * | 11/1967 | Misevich et al. | ......... 73/335.04 |
| 3,802,268 | A | * | 4/1974 | Thoma | ..................... 73/335.04 |
| 4,164,868 | A | | 8/1979 | Suntola | |
| 4,277,742 | A | * | 7/1981 | Kovac et al. | ................ 324/689 |
| 4,419,021 | A | * | 12/1983 | Terada et al. | ............ 73/335.05 |
| 5,069,069 | A | | 12/1991 | Migagishi et al. | |
| 5,177,662 | A | * | 1/1993 | Thoma | ..................... 73/335.04 |
| 5,200,633 | A | * | 4/1993 | Dickert et al. | .............. 257/253 |
| 5,372,750 | A | | 12/1994 | Thoma | |
| 6,132,893 | A | * | 10/2000 | Schoning et al. | ........... 257/253 |

* cited by examiner

Primary Examiner—Hezron Williams
Assistant Examiner—André K. Jackson
(74) Attorney, Agent, or Firm—Dykema Gossett PLLC

(57) ABSTRACT

A humidity sensor element for a humidity sensing device includes a rigid, p doped silicon substrate, a non-porous terminal on one side of the substrate, a porous terminal on a second side of the substrate, and a layer of polyphenylsulfone between the porous terminal and the substrate. The sensor elements displays improved linear response with humidity changes and very low hysteresis.

18 Claims, 2 Drawing Sheets

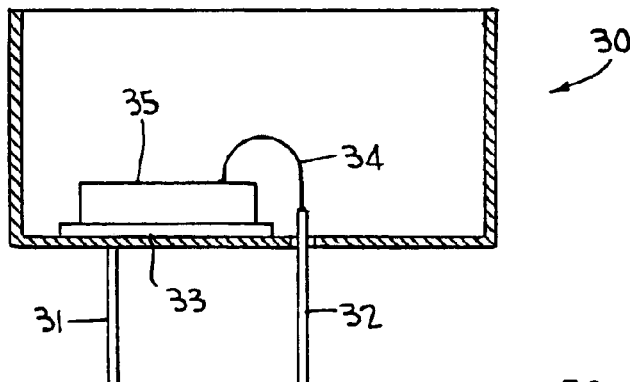
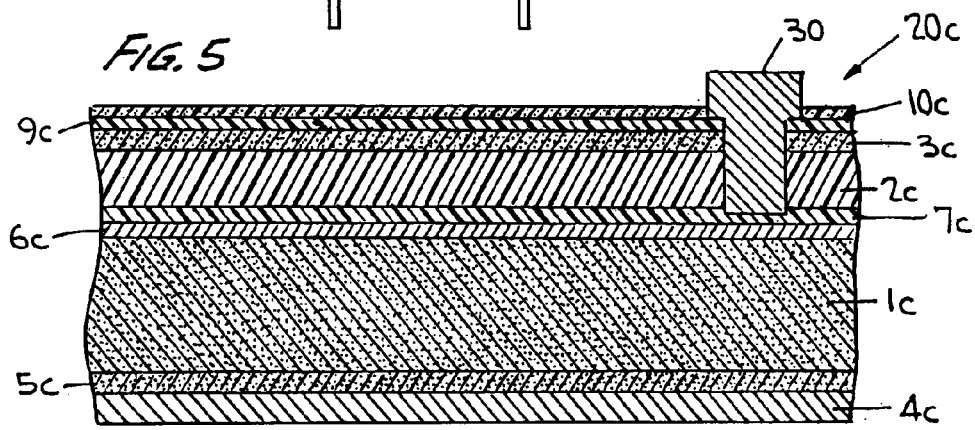
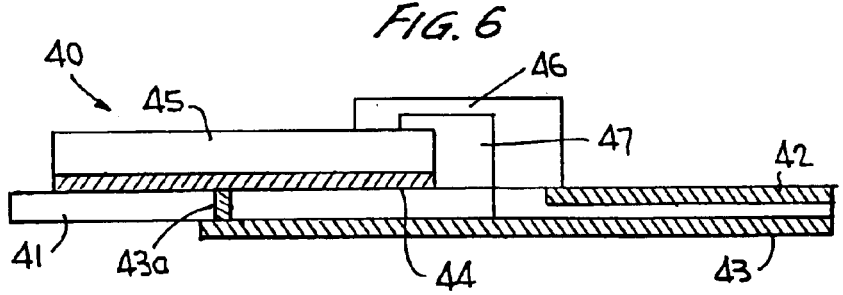
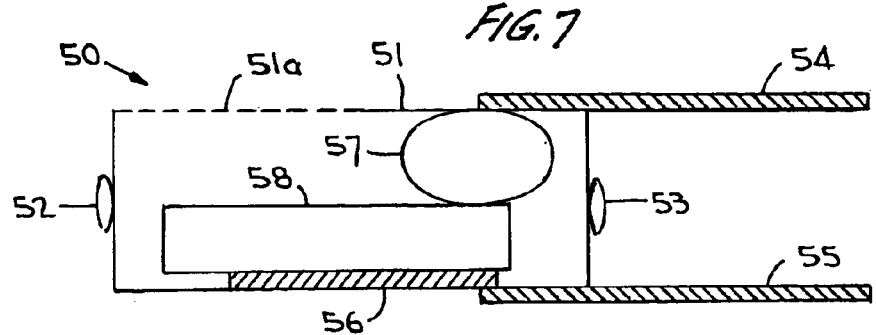

HUMIDITY SENSOR ELEMENT CONTAINING POLYPHENYLSULFONE

BACKGROUND OF INVENTION

1. Field of the Invention

The present invention relates to humidity sensor elements for use in humidity-sensing devices, and more particularly to humidity sensor elements containing sulfone polymers.

2. The Prior Art

Moisture-sensing devices which detect humidity levels by measuring the electrical capacitance of moisture-sensing elements containing sulfones are known. For example, U.S. Pat. No. 5,069,069 discloses moisture-sensing devices containing moisture-sensing films whose active layer is composed of either polyethersulfone or polysulfone. Although such known moisture-sensing devices work reasonably well, there is always a need to find alternative moisture-sensing polymers for use in moisture-sensing elements that will have more favorable physical and chemical characteristics, such as a more linear response with change in bulk dielectric constant with relative humidity, and thus provide a better functioning moisture-sensing device. I have discovered such an element.

SUMMARY OF INVENTION

According to my invention, a moisture or humidity sensor element for use in a moisture or humidity-sensing device includes polyphenylsulfone as its sensor polymer. Due to the advantageous properties of polyphenylsulfone such as solvent resistance and hydrolytic stability, the sensor element will display almost linear changes in dielectric constant with moisture level variation, and devices using the sensor element will display very low hysteresis and a low time constant (about 20 seconds at room temperature with hysteresis at 1% RH).

The inventive sensor element includes a rigid conductive substrate, a non-porous terminal layer on one side of the substrate, a porous or permeable terminal layer on a second side of the substrate, and a layer of polyphenylsulfone between the substrate and the porous terminal layer. The rigid, conductive substrate is advantageously made of p-doped silicon and the non-porous terminal layer is advantageously made of dual layers of gold and chromium. The porous terminal layer is made of gold, dual layers of gold and chromium, or a composite layer of lampblack and a binder which is permeable to water vapor and at least partially miscible in polyphenylsulfone.

For enhanced physical characteristics of the sensor element, including adhesion of the layers and integrity of the polyphenylsulfone layer, the doped silicon substrate is covered on both sides with a layer of silicon oxide. Other polymeric adhesion layers can be advantageously located between the polyphenylsulfone layer and the silicon oxide layer, and between the polyphenylsulfone layer and the porous terminal layer.

The invention will be better understood by reference to the attached drawings, taken with the following discussion.

BRIEF DESCRIPTION OF DRAWINGS

In the drawings,

FIG. 4 is a schematic illustration of first humidity sensor apparatus which utilizes the humidity sensor elements of FIGS. 1 or 2, FIG. 5 is a cross section of a humidity sensor element as shown in FIG. 2 when modified to work in the FIG. 4 apparatus, FIG. 6 is a schematic illustration of a second humidity sensor apparatus which utilizes the humidity sensor elements of FIG. 1, 2 or 3, and FIG. 7 is a schematic illustration of a third humidity sensor apparatus which utilizes the humidity sensor elements of FIG. 1, 2 or 3.

DETAILED DESCRIPTION

Figure 1:
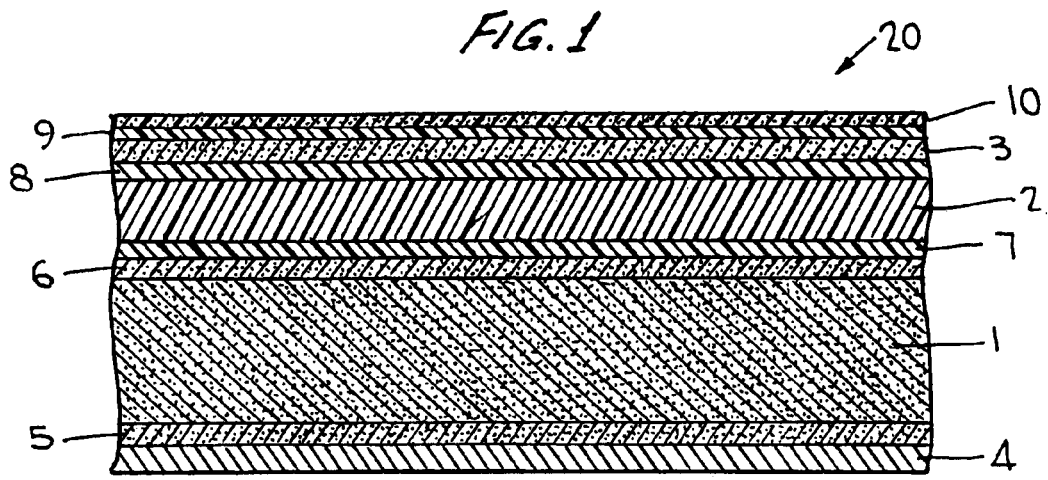
FIG. 1 shows, an enlarged scale, a cross section of a humidity sensor element in accordance with a first preferred embodiment of the invention.
Figure 2:
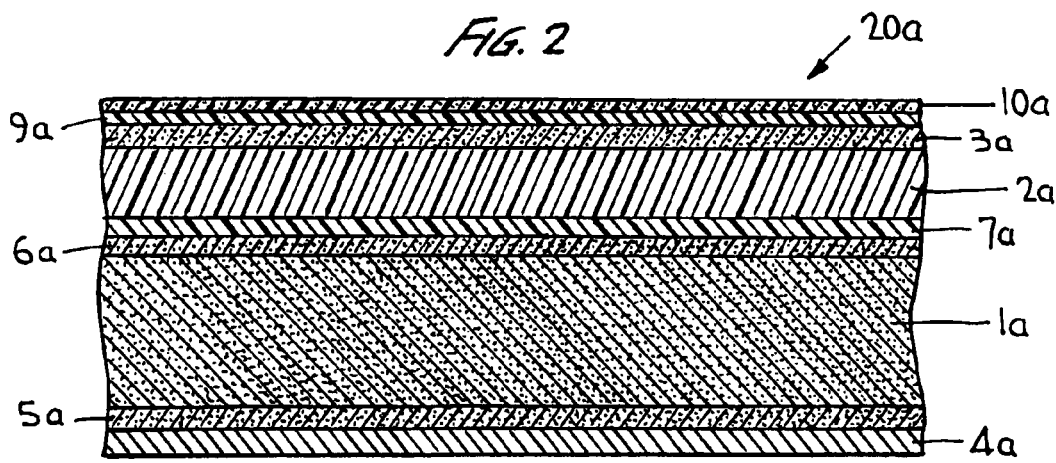
FIG. 2 is a cross section similar to FIG. 1 of a humidity sensor element in accordance with a second preferred embodiment.
Figure 3:
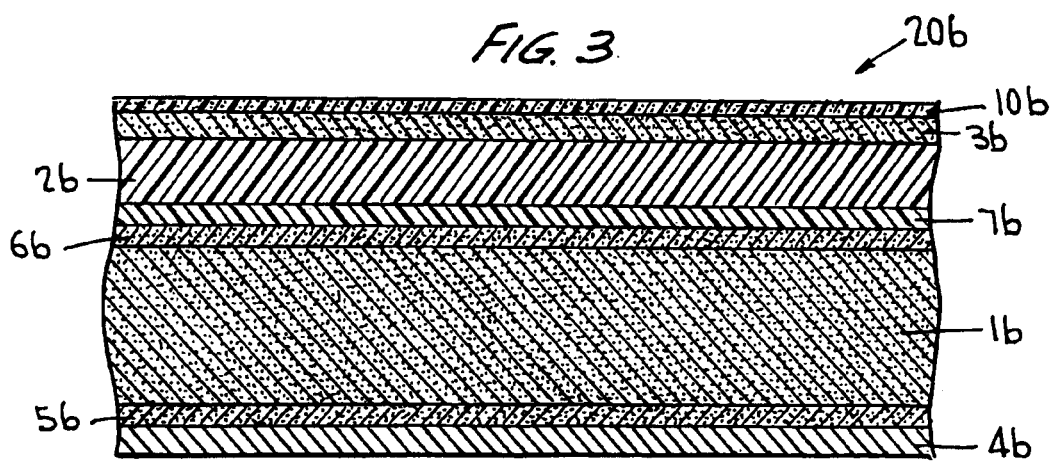
FIG. 3 is a cross section similar to FIG. 1 of a humidity sensor element in accordance with a third preferred embodiment.

FIGS. 1, 2 and 3 show cross sections through three preferred humidity sensor elements of the present invention. In the following discussion the terms "above" and "below" will be used based on relative vertical positionings as shown in FIGS. 1, 2 and 3.

Referring first to FIG. 1, the sensor element 20 is seen to include a rigid conductive substrate 1 made of doped silicon, a humidity sensor layer 2 of polyphenylsulfone located above the substrate, a terminal layer 3 of porous gold located above the sensor layer 2, and a non-porous terminal layer 4 of a chromiumgold composite located below the substrate 1. The terminal layers 3 and 4 are intended for connection to the leads of a humidity testing circuit. The pores in the gold terminal layer 3 are sufficiently large to allow passage of water vapor molecules therethrough for contact with the sensor layer 2. This is achieved by vapor deposition of the gold under controlled conditions. The polyphenylsulfone layer is between about 1 and 3 microns in thickness.

A first adhesion layer 5 of silicon oxide is located below the substrate 1 and between the substrate and the terminal layer 4 to adhere the terminal layer to the substrate. A second adhesion layer 6 of silicon oxide is located above the substrate 1 and below a layer 7 formed of an aminosilane or amino polyamic acid, which layer 7 also acts as an anchoring layer between the sensor layer and the substrate. The silicon oxide layers 5 and 6 can be thermally grown on the substrate 1. The layer 7 can be formed by coating layer 6 with either aminopropylsilane followed by a 1–3% solution of polyamic acid to form polyimide (Dupont Series PI2000 or PI2600). The polyimides form covalent bonds with the substrate 1 via the aminopropylsilane layer and are miscible in polyphenylsulfone.

Located between the sensor layer 2 and the terminal layer 3 is an anchoring layer 8 of mercaptopropylsilane. This layer is needed because the gold terminal layer 3 does not attach well to the polymeric sensor layer 2. A further layer 9 of mercaptopropylsilane is located above the terminal layer 3 to help attach an electrical lead to the terminal layer, as well as an applied water vapor-permeable barrier coating 10. This barrier coating can be in the form of polysulfone applied from a butyrophenone-acetone solution.

The sensor element 20a of FIG. 2 includes a rigid conductive substrate 1a of doped-silicon and layers 2a, 3a, 4a, 5a, 6a, 7a and 10a similar to layers 2–7 and 10 in the FIG. 1 embodiment; however, the porous terminal layer 3a is made of dual layers of chromium and gold (chromium deposition at 3–5 a/sec followed by gold at 3–4 a/sec), and no anchoring layer similar to layer 8 in FIG. 1 is included. The chromium-gold composite layer 3a is between about 400 and 700 angstoms in thickness.

The sensor element 20b of FIG. 3 includes a rigid conductive substrate 1c of doped silicon and layers 2b, 3b, 4b, 5b, 6b, 7b and 10b similar to layers 2–7 and 10 in the FIG. 1 embodiment; however, the water vapor-permeable terminal layer 3b is made of a composite of lampblack and a polymer binder. This layer can be formed from a mixture of lampblack and a binder of polyethersulfone, a soluble aramid (such as the condensation product of bis (4-aminophenyl) ether and isophthaloyl chloride), or a soluble polyimide (such as a condensation product of 3, 3', 4, 4' benzophenone tetracarboxylic diahydride and 5(6)-amnio-1-(4-aminophenyl)-1,3,3' trimethylindane in a suitable solvent such as dimethylsulfoxide, butryrophenone, tetrahydrofuran, 1-4dioxane, acetophenone, cyclohexanone, m-cresol or butyrolactone. No attachment layer similar to layer 9 is needed. The terminal layer 3b is between about 5 and 25 microns in thickness.

FIGS. 4, 6 and 7 depict embodiments of humidity sensor devices in which the inventive humidity sensor elements of this invention can be used. In FIG. 4 a conventional T05 can 30 with connectors 31 and 32 includes a sensor element 35 according to the present invention (either sensor element 30 or 30a) located on a flat mounting plate 33, a lead wire 34 from connector 32 being attached (bonded) to upper terminal layer of the sensor element, while the lower terminal layer is connected to the connector 31 by a layer of conductive epoxy (not shown). For best results, when the humidity sensor element of FIG. 1 is used in the humidity sensor device of FIG. 4, it is modified to include a gold via 30 for attachment of a lead (not shown) to the element, the gold via 30 extending from above the barrier coating 10c through the polymeric anchoring layer 9c, and through the sensor layer 2c (see FIG. 5) so as to provide an adequate and durable connection of the lead to the element 20c. The via can cover between 1 and 5% of the surface area of the terminal 3c and be provided by vapor deposition of gold (5,000–10,000 angstroms).

In FIG. 6 the sensor apparatus 40 includes an alumina substrate 41, conductive traces 42 and 43 (for connection to a lead frame), and a conductive mounting plate 44 on which a sensor element of the present invention (either sensor element 30, 30a or 30b) is positioned. A portion 43a of trace 43 extends through the alumina substrate 41 to attach to the lower terminal of the sensor element, while a conductive stitch 46 that extends around an insulating stitch 47 connects the upper terminal of the sensor element to the conductive trace 43.

In FIG. 7 the sensor apparatus 50 includes a mold 51 having hinges 52, 53 and a porous roof 51a, lead frames 54 and 55, and a conductive mounting plate 56 on which a sensor element 58 of the present invention (either sensor element 30, 30a or 30b) is positioned. The lead frame 55 is electrically connected to the mounting plate 56, which in turn is electrically connected to the lower terminal layer of the sensor element. A contact spring 57 is positioned between the sensor element 58 and the lead frame 54 to electrically connect the upper terminal layer thereof with the lead frame 54.

Although various preferred embodiments of the invention have been shown and described, modifications can be made therein and still fall within the scope of the appended claims. For example, the barrier layer can be excluded from the inventive sensor element when used in certain sensor apparatus, e.g., the sensor apparatus of FIG. 4.

What is claimed is:

1. A sensor element for measuring humidity and which comprises a substrate of doped silicon, said substrate defining opposite first and second sides; a non-porous first terminal layer located on said first side of said substrate; a porous or permeable second terminal layer located on said second side of said substrate; and a humidity-sensitive sensor layer located between said substrate and said second terminal layer, said sensor layer comprising polyphenylsulfone.

2. A sensor element according to claim 1, wherein said non-porous first terminal layer is composed of dual layers of chromium and gold.

3. A sensor element according to claim 2, including a first layer of silicon oxide located between said substrate and said first terminal layer for adhering said first terminal layer to said substrate.

4. A sensor element according to claim 3, including a second layer of silicon oxide located between said substrate and said sensor layer for adhering said sensor layer to said substrate.

5. A sensor element according to claim 4, including an anchoring layer between said second layer of silicon oxide and said sensor layer.

6. A sensor layer element according to claim 5, wherein said anchoring layer comprises aminosilane.

7. A sensor layer element according to claim 5, wherein said anchoring layer comprises an amino polyamic acid.

8. A sensor element according to claim 5, wherein said second terminal layer is made of gold.

9. A sensor element according to claim 8, including an anchoring layer of tetraethyoxysilane/mercaptosilane between said sensor layer and said second terminal layer.

10. A sensor element according to claim 5, wherein said second terminal layer is made of dual layers of chromium and gold.

11. A sensor element according to claim 5, wherein said second terminal layer is formed of lampblack in a binder.

12. A sensor element according to claim 11, wherein said binder is selected from the group consisting of polyethersulfone, a soluble aramid and a soluble polyimide.

13. A sensor element according to claim 12, wherein said binder is a soluble aramid formed of a condensation product of bis(4-aminophenyl) ether and isophthaloyl chloride.

14. A sensor element according to claim 12, wherein said binder is a soluble polyimide formed of a condensation product of 3,3',4,4'-benzophenone tetracarboxylic diahydride and 5(6)-amino-1-(4-aminophenyl)-1,3,3'trimethylindane.

15. A sensor element according to claim 1, including a vapor-permeable coating layer covering said second terminal layer.

16. A sensor element according to claim 1, wherein said substrate is composed of p-doped silicon.

17. A sensor element according to claim 1, wherein said sensor layer is between about 1 and 3 microns in thickness.

18. A sensor element according to claim 1, wherein said sensor layer consist essentially of polyphenylsulfone.

* * * * *